United States Patent [19]

Sorbonne

[11] Patent Number: 4,517,971

[45] Date of Patent: May 21, 1985

[54] GUARD FOR VENIPUNCTURE SITE AND CATHETER RETAINER

[76] Inventor: Robert L. Sorbonne, 2466 Michigan Ave., Salt Lake, Utah 84108

[21] Appl. No.: 443,271

[22] Filed: Nov. 22, 1982

[51] Int. Cl.³ .............................................. A61M 5/00
[52] U.S. Cl. .................................... 128/133; 604/174; 128/DIG. 6
[58] Field of Search ................... 128/132 R, 133, 154, 128/DIG. 6; 604/174–180

[56] References Cited

U.S. PATENT DOCUMENTS

| 2,367,690 | 1/1945 | Purdy | 128/154 X |
| 3,194,235 | 7/1965 | Cooke | 128/132 R |
| 3,722,508 | 3/1973 | Roberts | 128/133 |
| 3,900,026 | 8/1975 | Wagner | 128/133 |
| 4,316,461 | 2/1982 | Marais et al. | 128/133 X |

Primary Examiner—Dalton L. Truluck
Attorney, Agent, or Firm—Lynn G. Foster

[57] ABSTRACT

A device for protecting a venipuncture site and retaining a catheter and intravenous tubing at said site, without binding said catheter and tubing or occluding the flow therethrough. Easy accessibility to the venipuncture site and retention site is provided by a hinged cover. Much pain and discomfort associated with frequent removal of adhesive tape from a patient's skin, repeated venipuncture and trauma due to irritation caused by inadvertent catheter movement are eliminated or substantially eliminated because the catheter is disposed in a protective environment.

5 Claims, 9 Drawing Figures

GUARD FOR VENIPUNCTURE SITE AND CATHETER RETAINER

BACKGROUND

1. Field of Invention

The present invention relates generally to the field of intravenous catheters and more particularly to a novel guard for a venipuncture site and catheter and intravenous tubing retainer.

2. Prior Art

When intravenous fluid is to be injected into a patient periodically over a long period of time, the usual practice is to insert a cannula beneath the surface of the skin into a vein and then hold the cannula in position by adhesive tape. While this simple arrangement is effective, problems arise in that the adhesive tape sometimes prevents visual inspection of the venipuncture site, often provides inadequate retention of the cannula as the patient moves or is moved, and is a source of irritation and trauma to the patient.

Separate venipuncture site guard devices have been designed which allow the venipuncture site to be visually inspected, however such devices do not provide ready accessibility at repeated intervals of time to said venipuncture site. Patents such as British Pat. No. 2,046,095; U.S. Pat. Nos. 2,367,690; 3,900,026; and 3,782,377 generally illustrate the prior art relating to such venipuncture site guards.

Other devices have been designed which tend to anchor the catheter or cannula and intravenous tubing, at least partially insulate opposing ends thereof from stress which might otherwise be imposed thereon. Patents such as Swiss Pat. No. 556,668; U.S. Pat. Nos. 4,029,103; 3,942,528; 3,918,446; 3,826,254; 3,630,195; 3,059,645; and 2,669,231 generally illustrate such prior art catheter anchoring devices.

The number of patents cited above dealing with the protection of a venipuncture site illustrate the need for a single device which effectively, reliably and inexpensively guards a venipuncture site and retains the catheter in its subcutaneous condition without occulsion thereof.

Prior art devices of the type referred to above have generally failed to provide a reliable venipuncture site guard which provides ready and repeated accessibility to the venipuncture site and allows the cannula at the venipuncture site to move independently of the site guard while protecting the site. Also needed, and not provided by the prior art, is a non-occluding retainer for catheters at a venipuncture site and intravenous tubing connected thereto, preventing the binding or crimping when subjected to exterior stress, allowing high visibility of the catheter providing easy and repeated accessibility to the catheter and tubing via a latched access cover and permitting the catheter and the tubing to be removed and changed without requiring removal of the retainer itself.

BRIEF SUMMARY AND OBJECT OF THE INVENTION

In brief summary, the present invention relates to a venipuncture site guard and non-occluding catheter and intravenous tubing retainer, whereby many of the prior art problems mentioned above are either solved or substantially alleviated. The venipuncture site guard protects the penetration site and shields the cannula from inadvertent displacement, for example, while nurses move the patient and when an unconscious patient thrashes about. The catheter retainer insulates the cannula at the venipuncture site and the tubing from tension or other stress exerted upon the exposed portion of the intravenous tubing, providing an added measure of protection at the venipuncture site.

The device is preferably constructed of a semi-soft, flexible and clear synthetic resinous material which retains its shape. The device preferably has a crown and arches to prevent pressure from being exerted on an underlying vein and/or catheter and subsequent occlusion of fluid flow therethrough.

The crown or window of the device disposed over the venipuncture site is preferably hinged to rotate between open and closed positions. A latch releasably holds the cover in the closed position. The base of the guard is generally flat and circumscribes the venipuncture site in contiguous relation with the skin of the patient except for a bridging site over the vein. The cover is also ventilated to allow air to circulate over the venipuncture site and within the cavity formed by the guard.

The device is normally initially situated over the venipuncture site after the cannula has been inserted into the vein. Once the device is in place, it is attached by adhesive strips or tape.

When the guard portion is finally located and secured over the venipuncture site, the cannula is not restricted from moving with the patient. This is because the guard protects the venipuncture site and cannula from inadvertent external contact. The guard also preserves the cleanliness of said site while simulataneously making it readily accessible for inspection by medical personnel.

The catheter retainer also restricts inadvertent movement of the cannula and intravenous tubing and prevents unintentional withdrawal of the cannula from the venipuncture site.

The retainer serpentinely receives the tubing around posts sized so that the wound tubing absorbs tension placed thereon without crimping or occluding the flow of fluid therethrough.

The guard and retainer are typically used in combination but may be used separately so as to be placed over an indwelling cannula and/or in conjunction with IV tubing and there secured for a relatively long period of time. The snap down cover drastically reduces the pain and discomfort associated with indwelling catheter use.

With the foregoing in mind, it is a primary object of the present invention to provide a novel venipuncture site guard.

A principal object of the present invention is to provide a novel retaining device preventing dislodgement or crimping of a cannula.

An important object of the present invention is to provide a novel protective device comprising a cover which may be moved to allow repeated access to the venipuncture site.

A further paramount object of the present invention is to provide a novel venipuncture site guard allowing ventilation of the venipuncture site and surrounding tissues.

Another principal object of the present invention is to provide a novel protective device wherein the cover means may be manually open and shut.

Another important object of the present invention is to provide a novel protective device which is arcuately constructed of semi-soft and flexible material so that pressure on the underlying vein, catheter and tubing will be substantially avoided and occlusion of fluid flow through said vein, catheter and tubing prevented.

A further dominant object is the provision in combination of a novel catheter guard and a retainer for intravenous tubing.

These and other objects and features of the present invention wlil be apparent from the following detailed description, taken with reference to the accompanying drawings.

DETAILED DESCRIPTION OF THE ILLUSTRATED EMBODIMENTS

Figure 1:
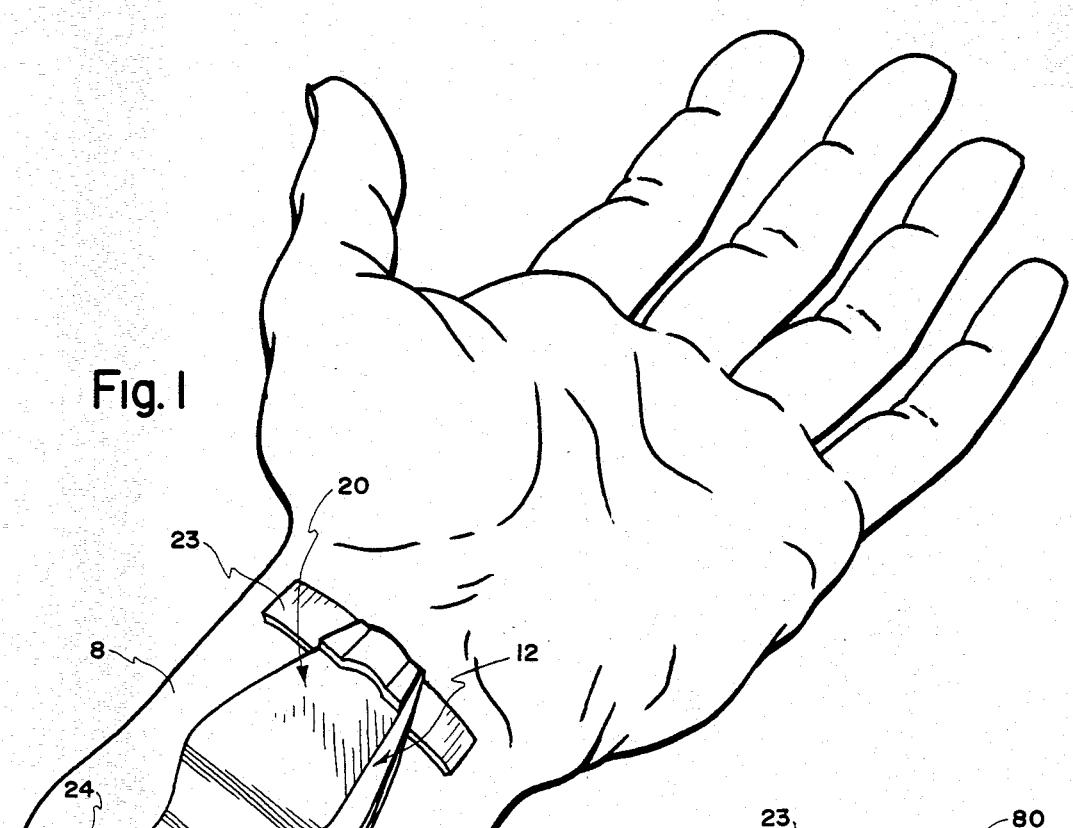
FIG. 1 is a fragmentary perspective representation of a presently preferred venipuncture guard retainer in accordance with the present invention illustrated in its installed position on the wrist of a patient.
Figure 2:
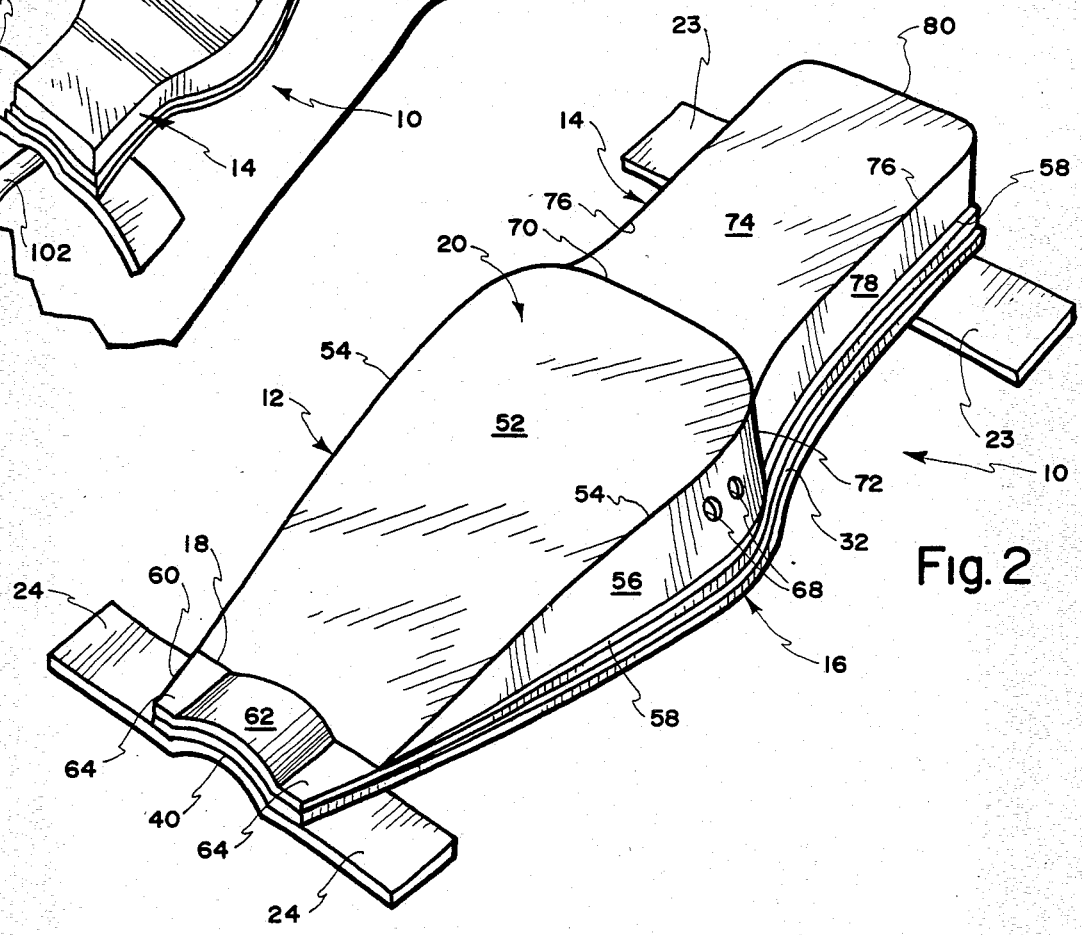
FIG. 2 is an enlarged perspective representation of the venipuncture guard retainer of FIG. 1 in its uninstalled condition.

Reference is now made to the accompanying drawings wherein like numerals are used to designate like parts throughout. FIGS. 1-8 illustrate a combination device comprising a venipuncture site guard and a catheter and IV tubing retainer, generally designated 10. Device 10 is preferably formed of semi-soft, flexible, clear, shape-retaining synthetic resinous material using conventional molding techniques. Device 10 comprises two distinct though integral sections, i.e. a venipuncture site guard section and a catheter and tube retaining section, generally designated 12 and 14, respectively. Device 10 can also be used in conjunction with urinary drainage tubes. The size of device 10 may vary depending on intended use.

The device 10 comprises a base 16, an openable cover or lid 20 (which is hinged at site 18) and forward and rearward adhesive strips 23 and 24, respectively.

Placement of the device 10 on the wrist of a patient 8 using the adhesive strips 23 and 24 is illustrated, by way of example, in FIG. 1. It should be readily apparent that the device 10 may be used at other sites on the body of the patient.

Figure 3:
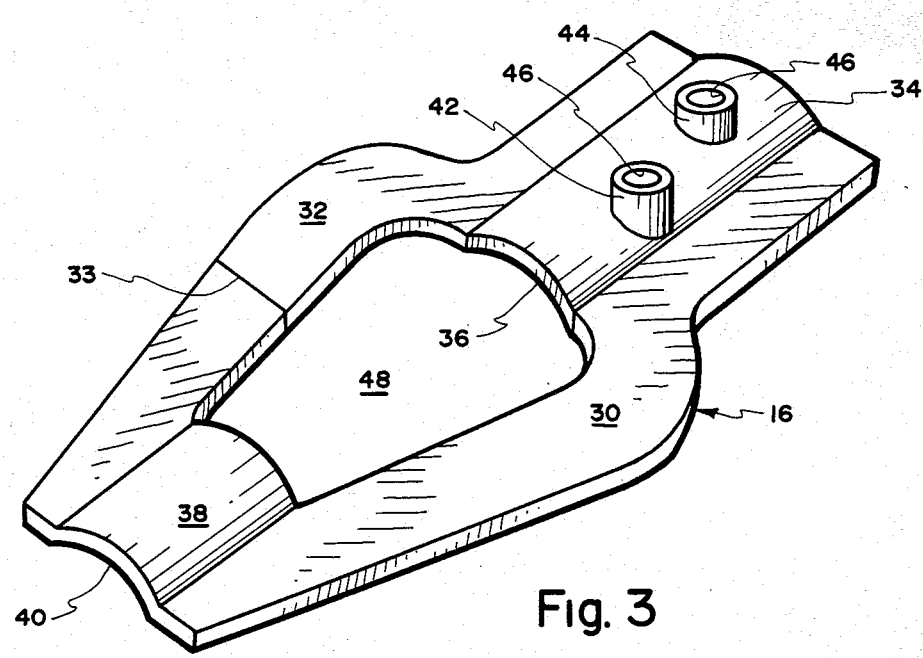
FIG. 3 is a perspective representation of the base of the guard/retainer of FIG. 1.

More specifically, the base 16 comprises a generally arrow shaped substantially planar shape-retaining part, best illustrated in FIG. 3. Base 16 is preferably formed of one piece molded construction using synthetic resinous material and is, preferably, transparent. The base 16 comprises flat opposed side flanges 30 and 32 disposed in a common plane.

In those situations where it is desired to place the device 10 over an existing venipuncture site having an indwelling cannula, it is presently preferred that one of the flanges 30 or 32 be severed midway along the opening 48. In this regard, reference is made to FIG. 3, which illustrates such a slit 33 across flange 32. By relatively displacing the portions of flange 32 adjacent the slit 33 with the cover open, the existing indwelling cannula and/or intravenous tubing connected thereto may be passed through the gap so created at slit 33 to correctly position the device 10 around the existing venipuncture site. Thereafter a suitably sized piece of adhesive tape or the like can be placed along flange 32 over slit 33 to retain the base 16 in the configuration shown in FIG. 3.

A forward arch 34 bridges between the flanges 30 and 32 and defines an arched cavity 36 thereunder. Likewise, a bridge 38 integrally spans between the flanges 30 and 32 at the trailing ends thereof to define an arched cavity 40 thereunder. The base 16 is illustrated as being of uniform relatively narrow thickness throughout.

The bridge 34 defines two offset and integral hollow spools or annular cylindrical anchors 42 and 44, each of which projects generally perpendicular to the plane containing flanges 30 and 32. The anchor spools 42 and 44 are illustrated as each having the same outside diameter and each defining a hollow circular interior 46 of equal radius. The spools 42 and 44 serve to restrain IV tubing and to latch the lid 20, as hereinafter more fully described.

The base 16 also defines an interior opening or window 48 to accommodate placement of the base 16 around a venipuncture site, as hereinafter more fully described.

The cover or lid 20, when in the assembled and closed condition, comprises a dome which defines a hollow interior 50 (FIGS. 7 and 8) and comprises, at section 12, a sloped top wall 52, integral at elevated corners 54 and with spaced tapered sidewalls 56. Sidewalls 56 terminate in lower side flanges 58, which rest (when the cover 20 is closed) contiguously upon the top surface of flat sides 30 and 32 of the base 16. Since the flanges 30 and 32 extend beyond flanges 58, a lip exists where flanges 30 and 32 are so exposed. The lid 20 is generally of uniform narrow thickness throughout. The flanges 58 strengthen the cover 20.

The top surface 52, the corners 54 and the sidewalls 56 are sloped to a common line of termination 18 which comprises a reduced thickness living hinge or fold line in the synthetic resinous material from which the cover 20 is made (preferably clear polyethylene) without opening the cover. When the cover 20 is clear, the venipuncture site, catheter and tubing may be visually inspected. The flanges 58 merge rearward at fold line 18 with an attachment flap 60. Attachment flap 60 comprises an arch 62 flanked by integral flat walls 64. Arch 62 and flat walls 64 are sized and shaped to be completely contiguous with arch 38 and the juxtaposed portions of side flanges 30 and 32 of the base 16. Thus, an interface 66 between the attachment flap 60 and the juxtaposed portions of the base 16, at which interface the two parts are secured together by bonding, plastic welding or the like.

Thus, the cover 20 may be manually opened and closed by a pivotal or hinged action at line 18.

The sidewalls 56 are illustrated as comprising a plurality of apertures 68 for purposes of providing appropriate ventilation to the interior of the device 10 when installed and in the closed position. The arches 34 and 38 of the base 16 also may aid in providing some air circulation and ventilation.

Having described that portion of the cover 20 at section 12 (adapted to conceal and enclose the venipuncture guard section), attention is now directed to the portion of cover 20 which is adapted to conceal the retainer section 14. More specifically, adjacent the crown 70 of the cover 20 comprises a forward surface 72. Adjacent the intermediate forwardly facing surface 72 is a necked down forward portion of the cover 20 which continues the hollow interior 50, but of smaller size. Forward portion of the cover 20 comprises a top generally horizontal surface 74 which merges with surface 72 and further merges at elevated corner 76 with sidewalls 78 which are substantially perpendicular to surface 74 and flanges 30 and 32. The sidewalls 78 merge with the sidewalls 56 of the cover 20 adjacent forward face 72, all said merges being integral since the cover 20 is illustrated as being of one piece construction. Top wall 74, sidewalls 78 and corners 76 integrally merge with front perpendicular wall 80. The sidewalls 78 integrally merge with previously mentioned flanges 58. The lower edge of front wall 80 merges in aligned relation with the lower surface of the flanges 58 and is also contiguous with previously mentioned arch 34 of the base 16 when the lid 20 is closed. Thus, the lower edge of front wall 80 and the flanges 58 form a snug relationship with the top of previously described base 16.

Figure 8:
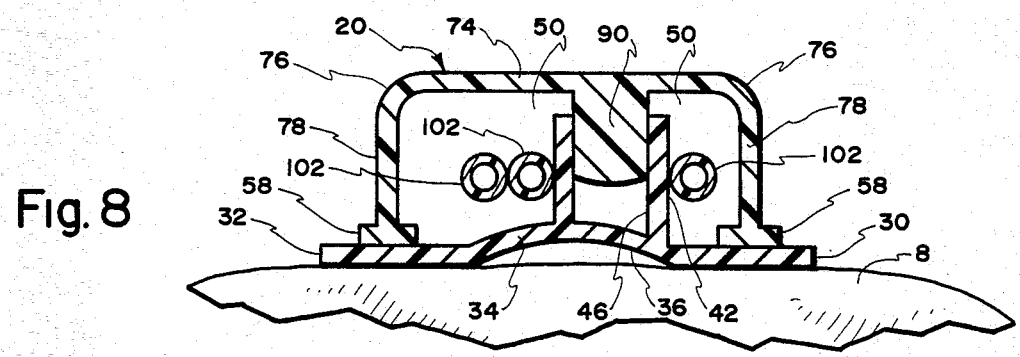
FIG. 8 is a cross sectional view taken along line 8—8 of FIG. 4.

Two downwardly projecting cylindrical studs or posts 90 are integral with the top cover walls 74, are perpendicular thereto and project into hollow cavity 50. Each stud 90 is sized and located so as to be in alignment with the previously described annularly hollow spools 42 and 44. Thus, the studs 90 fit within the hollow interior 46 in snug tight-fitting though releasable relation when the cover is in a closed position to form a snap or friction latch as best illustrated in FIG. 8. The friction latch can be readily overcome by manual force to open the cover 20. The cover 20 may be held in its releasable, closed position in other ways, such as by use of Velcro.

While adhesive strips 23 and 24 are illustrated and described it is to be appreciated that separate pieces of adhesive tape or other forms of attachment could be used for securing the device 10 to the skin of the patient 8 during use. Preferably, adhesive strips 23 and 24 have a bonding agent or the like along the top surface where each tape is contiguous with the arch 38 and adjacent portions of flanges 30 and 32 of the previously described base 16 so that a dependable connection is achieved as illustrated in the Figures. The lower surface of the adhesive strips 23 and 24 comprises a suitable layer of adhesive which, prior to use, may be covered by an appropriate peel-off layer or backing to prevent contamination of the adhesive prior to use as is conventional.

Figure 4:
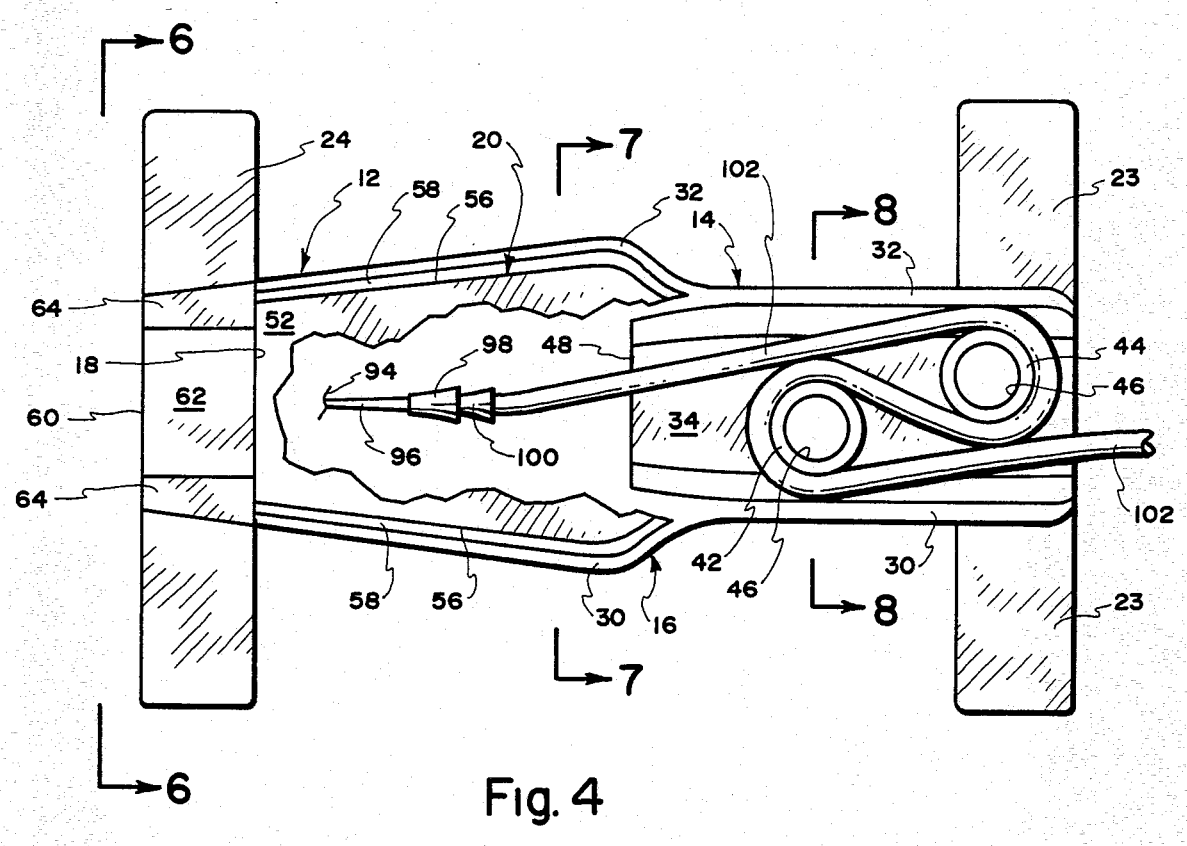
FIG. 4 is a plan view of the venipuncture guard retainer of FIG. 1 in its installed position with part of the lid broken away for clarity of illustration.
Figure 5:
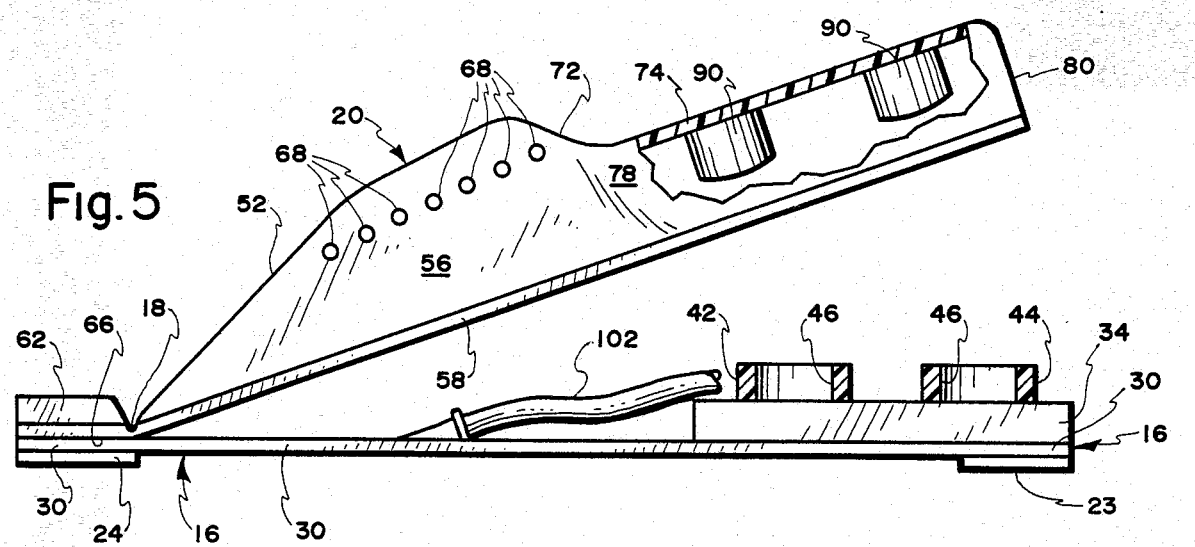
FIG. 5 is a side elevation of the venipuncture guard retainer of FIG. 1 with the lid in a partially open condition.
Figure 6:
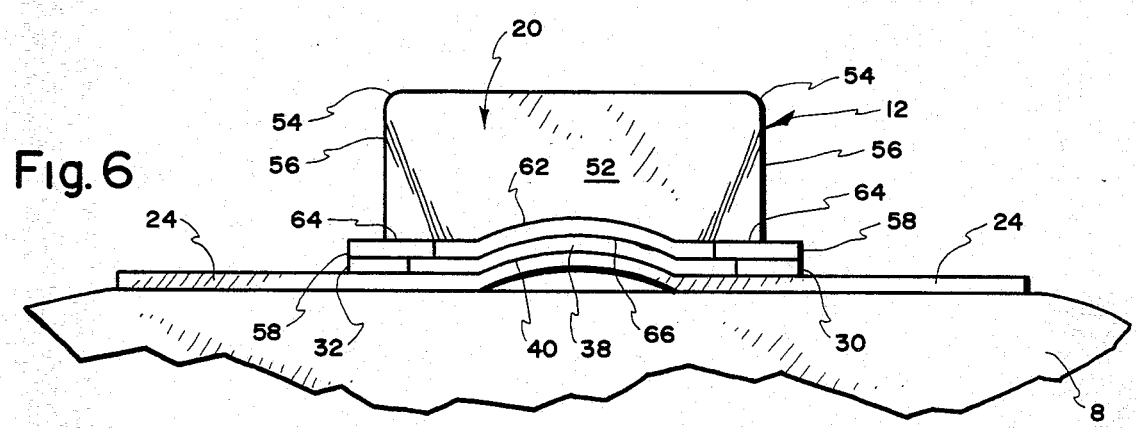
FIG. 6 is an end elevation taken along lines 6—6 of FIG. 4.
Figure 7:
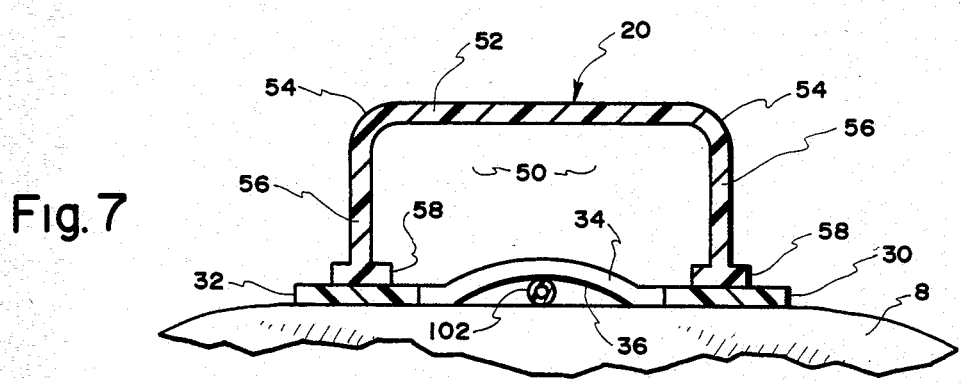
FIG. 7 is a cross sectional view taken along line 7—7 of FIG. 4.

In use, ordinarily the doctor or other medical personnel will insert a needle or a catheter-bearing needle into a vein of the patient 8 at venipuncture site 94 (FIG. 4). The needle or plastic catheter tube 96 is left indwelling and serves as a cannula for repeated, continuous, successive and/or intermittent fluid flow (into or out of the vein). The cannula 96 typically terminates in a hub 98 which is connected at fitting 100 to a length of intravenous tubing 102.

Once the cannula 96 has been placed in the vein of the patient 8 at venipuncture site 94 and before the fitting 100 is attached to hub 98, the device 10 is placed over the venipuncture site 94 so that opening 48 centrally surrounds the venipuncture site 94. The adhesive strips 23 and 24 are secured firmly to the skin of the patient 8 and the cover 20 is manually opened as previously described. The fitting 100 is then connected to the hub 98 and the intravenous tubing 102 threaded around the cylindrical posts 42 and 44 in the manner illustrated in FIG. 4. This insulates the cannula from external stress (tension) inadvertently applied to the tubing 102 outside the device 10 while preventing crimping or occlusion of the tubing 102. The tubing 102 is typically connected to an intravenous bottle or the like as is customary.

The cover 20 is next displaced from its open to its closed position causing the studs or posts 90 to be firmly press fit in releasable fashion into the hollow interiors 46 of the spools 42 and 44.

Thus, the venipuncture site 90 is protected against inadvertant contact or catheter displacement while accommodating repeated visual inspection of the venipuncture site, the cannula and the tubing.

Ready and repeated access to the interior of the device 10 and the venipuncture site 94, the cannula 96 and the intravenous tubing 102 may be facilely achieved by merely manually opening the cover to force remove the studs 90 from within the hollow interiors 46 of the spools 42 and 44.

Figure 9:
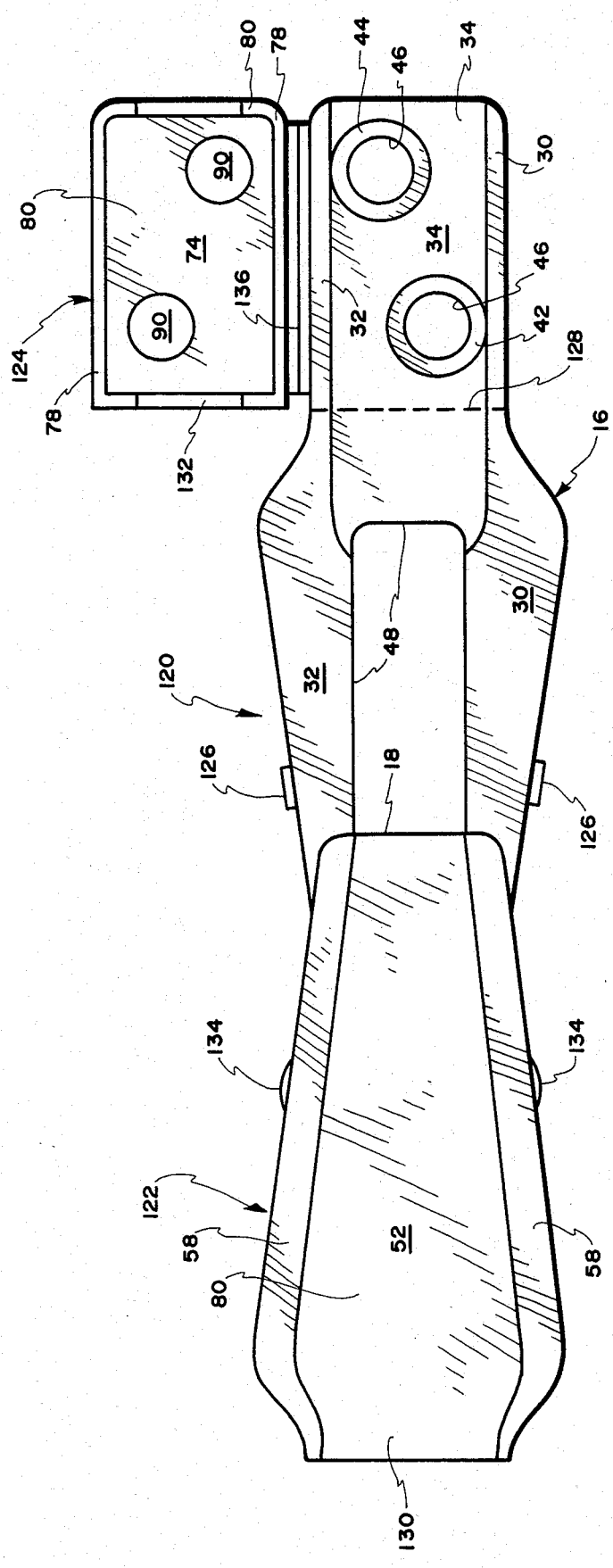
FIG. 9 is a plan view of a second presently preferred venipuncture guard retainer in accordance with the principals of the present invention illustrating two access lids in their open positions.

Reference is now made to FIG. 9, which illustrates a second presently preferred intravenous guard/retainer device, generally designated 120. The device 120 differs from the device 10 heretofore described principally in that the venipuncture guard section 12 is concealed by one cover, generally designated 122 and the retainer section 14 by a second cover, generally designated 124. For ease of illustration, the device 120 is not shown as having adhesive strips.

Base 16 comprises a pair of resilient upwardly directed tabs 126 integral with the sides 30 and 32 of the base. The cover 122 is substantially identical to the trailing portion of cover 20 heretofore described up to a site or line 128 (FIG. 10) where cover 122 terminates at forward lip 130. The lip 130 is transverse to the axis of the device 120 and designed to be, in its closed position, beneath the flange 132 of cover 124 and contiguous with arch 34.

Along the exterior surface of sidewalls 56 of cover 122 comprise protrusions 134, in alignment with and sized and shaped so as to outwardly displace resilient fingers 126 to thereby frictionally retain the cover 122 in its closed position against inadvertent displacement.

The cover 124 is substantially identical to the forward portion previously described cover 20 and comprises top surface 74, side surfaces 78 and wall 80 and studs 90. One of the walls 78 is illustrated as being secured by an integral plastic hinge 136 to the edge of base flange 32. Also, cover 124 comprises a rear wall 32, integral with top 74 and sides 78. The cover 124 is open and closed by pivoting the cover 124 along hinge 136, causing the studs 90 to be removed and inserted into press fit relation with the hollow interiors 46 of the spools 42 and 44.

Line 128 may be of reduced thickness accommodating total manual separation of sections 12 and 14 along the line 128 for separate use of each.

The invention may be embodied in other specific forms without departing from the spirit or essential characteristics thereof. The present embodiments are therefore considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by United States Letters Patent is;

1. A venipuncture guard for a medical patient comprising:

generally flat skin-engaging base means, the base means comprising an opening accommodating placement of the base means around a venipuncture site;

lid means comprising means bridging over the venipuncture site in spaced relation thereto comprising means for successively opening and means for closing the lid means in respect to the base means to permit access to the venipuncture site and conceal the site from debris and prevent inadvertent displacement of an intravenous cannula in respect to the vein of a patient at the venipuncture site, respectively;

the guard further comprising means defining passageway means by which medical tubing spans between the venipuncture site and the exterior of the guard;

the guard further comprising vein bridge means in aligned though axially spaced relation to the venipuncture site which vein means prevents occlusion by the guard of the vein in which the venipuncture site is disposed; and anti-displacement means, associated with the vein bridge means, which prevent inadvertent removal of an indwelling cannula from the venipuncture site.

2. A non-occluding, non-crimping retainer for use with an indwelling cannula and connected tubing in conjunction with a medical patient comprising:

generally flat skin-engaging base means having a venipuncture site opening disposed at a central site therein;

vein bridge means in the base means which prevent occlusion of the vein in which the venipuncture site is located;

passageway means associated with the vein bridge means accommodating passage of the intravenous tubing therethrough;

anti-displacement means disposed at a second site in close proximity to the passageway means and the vein bridge means and in alignment with the venipuncture site opening, which anti-displacement means securedly anchor the tubing adjacent the passageway means without occluding or crimping the tubing, the second site being in seriatum with the first site;

lid means comprising means for opening and means for closing the lid means in respect to the base means to respectively expose and conceal the venipuncture site and the tubing within the passageway means.

3. A retainer according to claim 2 wherein the anti-displacement means comprise means around which the tubing is wound to create at least one reverse curve in the tubing.

4. A non-occluding, non-crimping retainer for use with intravenous tubing and the like in conjunction with a medical patient comprising:

generally flat skin-engaging base means;

passageway means associated with the base means accommodating passage of the intravenous tubing therethrough;

anti-displacement means which securedly anchor the tubing within the passageway means without occluding or crimping the tubing;

lid means comprising means for opening and means for closing the lid means in respect to the base means to respectively expose and conceal the tubing within the passageway means, the closing means comprise releasable latch means, which latch means comprise mating male-female connectors, the connectors comprising annular means having hollow interior means and post means aligned with and sized to snugly frictionally engage the annular means within the hollow interior means thereof, the annular means and post means comprising at least two sets each of which presents two cylindrical surfaces comprising the anti-displacement means around which the tubing is wound.

5. A device which guards a venipuncture site of a medical patient and retains the position of intravenous tubing spanning from the venipuncture site to a location exterior of the device, the device comprising:

generally flat skin-engaging base means, the base means comprising an opening accommodating placement of the base means around the venipuncture site;

passageway means through which the intravenous tubing spans between the venipuncture site and a location exterior of the device;

anti-displacement means which securely anchor the tubing within the device against inadvertent displacement thereof without occluding or crimping of the tubing;

lid means comprising cavity-defining means bridging over the venipuncture site and the anti-displacement means, the lid means comprising means for successively opening and means for closing the lid means in respect to the base means to permit access to the venipuncture site, and conceal the site from debris and prevent inadvertent displacement of an intravenous cannula in respect to the vein of a patient at the venipuncture site, respectively, said lid means comprising first cover means bridging the venipuncture site and second cover means concealing the anti-displacement means.

* * * * *